United States Patent
Marik et al.

(10) Patent No.: US 8,425,562 B2
(45) Date of Patent: Apr. 23, 2013

(54) SYSTEMS AND DEVICES FOR DYNAMIC STABILIZATION OF THE SPINE

(75) Inventors: Greg C. Marik, Collierville, TN (US); Julien J. Prevost, Memphis, TN (US); Jayant Jangra, Memphis, TN (US); Henry K. Bonin, Jr., Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 303 days.

(21) Appl. No.: 12/422,367

(22) Filed: Apr. 13, 2009

(65) Prior Publication Data

US 2010/0262191 A1    Oct. 14, 2010

(51) Int. Cl.
*A61B 17/70* (2006.01)

(52) U.S. Cl.
USPC ............. 606/255; 606/257; 606/264

(58) Field of Classification Search .......... 606/246–279; 623/17.11–17.16
See application file for complete search history.

(56) References Cited

U.S. PATENT DOCUMENTS

| | | | |
|---|---|---|---|
| 5,480,401 A | 1/1996 | Navas | |
| 7,175,622 B2 | 2/2007 | Farris | |
| 7,291,150 B2 | 11/2007 | Graf | |
| 7,704,271 B2 | 4/2010 | Abdou | |
| 7,776,071 B2* | 8/2010 | Fortin et al. | 606/257 |
| 7,862,586 B2* | 1/2011 | Malek | 606/246 |
| 2004/0049190 A1 | 3/2004 | Biedermann et al. | |
| 2004/0143264 A1 | 7/2004 | McAfee | |
| 2004/0225289 A1 | 11/2004 | Biedermann | |
| 2005/0113927 A1* | 5/2005 | Malek | 623/17.16 |
| 2005/0261685 A1* | 11/2005 | Fortin et al. | 606/61 |
| 2006/0082987 A1 | 4/2006 | Dorsey et al. | |
| 2006/0113927 A1 | 6/2006 | Bondy et al. | |
| 2006/0229609 A1* | 10/2006 | Wang | 606/61 |
| 2006/0247637 A1* | 11/2006 | Colleran et al. | 606/61 |
| 2006/0264940 A1 | 11/2006 | Hartmann | |
| 2006/0293657 A1 | 12/2006 | Hartmann | |
| 2006/0293663 A1 | 12/2006 | Walkenhorst et al. | |
| 2007/0029362 A1 | 2/2007 | Caillaud et al. | |
| 2007/0049936 A1 | 3/2007 | Colleran et al. | |
| 2007/0078461 A1 | 4/2007 | Shulzas | |
| 2007/0100341 A1 | 5/2007 | Reglos et al. | |
| 2007/0161997 A1 | 7/2007 | Thramann et al. | |
| 2007/0233085 A1 | 10/2007 | Biedermann et al. | |
| 2007/0233091 A1 | 10/2007 | Naifeh et al. | |
| 2007/0270810 A1 | 11/2007 | Sanders | |

(Continued)

OTHER PUBLICATIONS

Response to Office Action for U.S. Appl. No. 12/422,387, filed Jun. 22, 2011.

(Continued)

*Primary Examiner* — Ellen C Hammond
*Assistant Examiner* — Atiya Mahmud

(57) ABSTRACT

A dynamic stabilization system for use with a spinal motion segment includes a first bone anchor assembly, a second bone anchor assembly, a resilient element, and a sheath. The resilient element includes an end portion engageable with the first bone anchor assembly and a resilient portion engageable with the second bone anchor assembly. The resilient element provides resilient resistance when the first and second bone anchor assemblies are moved toward one another and provides no resistance and is separable from the second bone anchor assembly when the first and second bone anchor assemblies are moved away from one another. The sheath surrounds the resilient portion and articulation surface of the second bone anchor assembly.

12 Claims, 16 Drawing Sheets

U.S. PATENT DOCUMENTS

| | | |
|---|---|---|
| 2007/0270814 A1 | 11/2007 | Lim |
| 2007/0270837 A1 | 11/2007 | Eckhardt et al. |
| 2007/0270838 A1 | 11/2007 | Bruneau et al. |
| 2007/0288009 A1 | 12/2007 | Brown et al. |
| 2008/0021459 A1 | 1/2008 | Lim |
| 2008/0039847 A1 | 2/2008 | Piper et al. |
| 2008/0065073 A1 | 3/2008 | Perriello et al. |
| 2008/0172091 A1* | 7/2008 | Anderson ............ 606/246 |
| 2008/0183213 A1 | 7/2008 | Veldman et al. |
| 2008/0195208 A1* | 8/2008 | Castellvi et al. ........ 623/17.15 |
| 2008/0262554 A1* | 10/2008 | Hayes et al. ............ 606/278 |
| 2008/0275504 A1* | 11/2008 | Bonin et al. ............ 606/246 |
| 2008/0300633 A1* | 12/2008 | Jackson ............ 606/257 |
| 2009/0105820 A1* | 4/2009 | Jackson ............ 623/17.11 |
| 2009/0228045 A1* | 9/2009 | Hayes et al. ............ 606/257 |
| 2009/0275986 A1* | 11/2009 | Prevost et al. ............ 606/278 |
| 2010/0004685 A1* | 1/2010 | Justis et al. ............ 606/246 |
| 2010/0042152 A1* | 2/2010 | Semler et al. ............ 606/250 |
| 2010/0262187 A1 | 10/2010 | Marik et al. |
| 2010/0262192 A1 | 10/2010 | Foley |

OTHER PUBLICATIONS

Response to Office Action for U.S. Appl. 12/422,606, filed Jun. 23, 2011.

* cited by examiner

SYSTEMS AND DEVICES FOR DYNAMIC STABILIZATION OF THE SPINE

CROSS-REFERENCE TO RELATED APPLICATIONS

This application is related to U.S. patent application Ser. No. 12/422,606 entitled "Systems and Devices for Dynamic Stabilization of the Spine," and U.S. patent application Ser. No. 12/422,387 entitled "Systems and Devices for Dynamic Stabilization of the Spine," filed on the same day as the present application, the entireties of both of which are incorporated herein by reference.

BACKGROUND

Elongated connecting elements, such as rods, plates, tethers, wires, cables, and other devices have been implanted along the spinal column and connected between two or more anchors engaged with one or more spinal motion segments. Some connecting elements provide a rigid construct that resists movement of the spinal motion segment in response to spinal loading or movement of the spinal motion segment by the patient. Still other connecting elements are flexible to permit at least limited spinal motion while providing resistance to loading and motion of the spinal motion segment. Such flexible connecting elements can be considered to provide dynamic spinal stabilization since at least limited movement of the spinal motion segment is preserved after implantation of the connecting element.

SUMMARY

The present invention generally relates to systems, devices, and methods for dynamically stabilizing a spinal column motion segment including at least two vertebrae by engaging a resilient element between the two vertebrae. An exemplary resilient element includes an end portion and a resilient portion positioned between the two vertebrae.

In one aspect a spinal stabilization system for dynamically stabilizing a first vertebral body with respect to a second vertebral body includes first and second anchor assemblies attachable to respective ones of the first and second vertebral bodies and a resilient element including an end portion and a resilient portion and having a length along a longitudinal axis sized for positioning between and engaging each of the first and second anchor assemblies when the first and second anchor assemblies are attached to the respective vertebral bodies. The resilient portion and the end portion are attached to each other. In one embodiment, the resilient element further includes a tether extending from the end portion through the resilient portion along the longitudinal axis, such as within axial bores of each of the end portion and resilient portion, to attach the resilient portion and the end portion.

In another aspect, a resilient element for stabilizing one vertebral body with respect to a second vertebral body in a dynamic spinal stabilization system includes an elongated body extending along a longitudinal axis that includes an end portion and a resilient portion attached to the end portion. The resilient portion and the end portion are attached to each other. The resilient element further includes a tether extending from the end portion through the resilient portion along the longitudinal axis, such as within axial bores of each of the end portion and resilient portion, to attach the resilient portion and the end portion.

In yet another aspect, a method for dynamic stabilization of a spine includes implanting a first anchor assembly into a first substrate, the first anchor assembly having a connector, and a second anchor assembly into a second substrate, the second anchor assembly having an articulation surface. A resilient element having and end portion and a resilient portion is positioned such that the end portion is connectable to the connector of the first anchor assembly and the resilient portion is engageable with the articulation surface of the second anchor assembly when the first anchor assembly and the second anchor assembly are moved closer to each other. The end portion is connected to the connector of the first anchor assembly.

These and other aspects are described below.

DESCRIPTION OF THE ILLUSTRATED EMBODIMENTS

Figure 1:
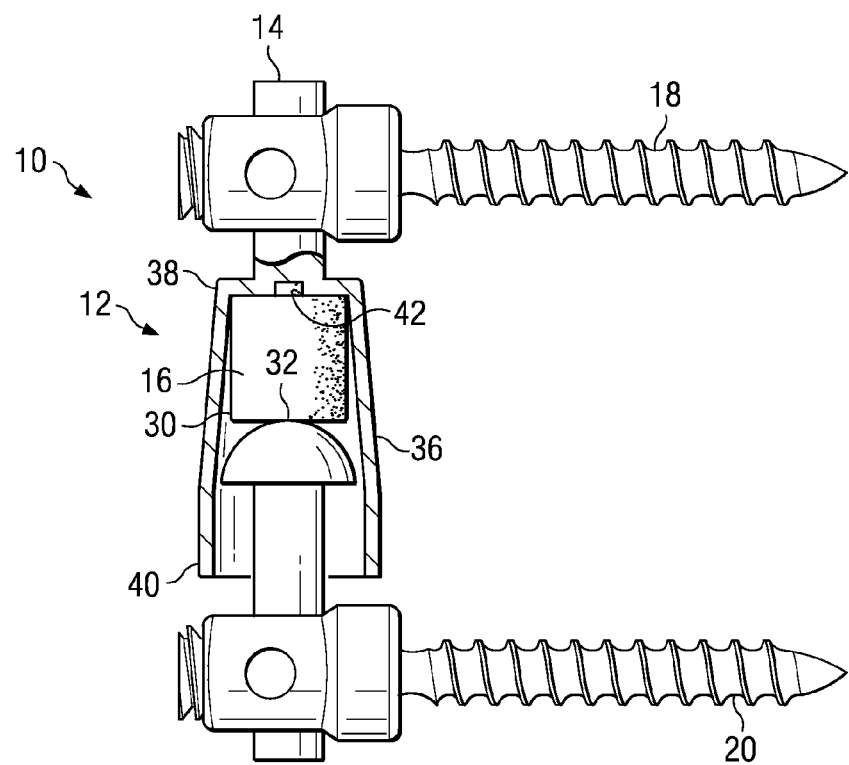
FIG. 1 is an elevational view, partially in cross section, of an embodiment of the present invention.

The present disclosure relates generally to the field of orthopedic surgery, and more particularly to systems and methods for stabilizing a spinal joint or spinal motion segment. For the purposes of promoting an understanding of the principles of the invention, reference will now be made to the embodiments illustrated in the drawings and specific language will be used to describe the same. It will nevertheless be understood that no limitation of the scope of the invention is thereby intended. Alterations and further modifications in the illustrated devices, as well as further applications of the principles of the invention as illustrated herein, are contemplated as would normally occur to one skilled in the art to which the invention relates.

Systems, devices, and methods for providing dynamic stabilization of one or more spinal motion segments are described. The systems and devices include a resilient element between at least two bone anchor assemblies that can be attached to at least two or more vertebral bodies of a spinal motion segment. The resilient element extends along a longitudinal axis and includes an end portion engageable to at least one of the anchor assemblies and a resilient portion attached to the end portion and separably engageable with an articulation surface of at least one of the bone anchor assemblies, the resilient member allowing movement of the vertebra to which the resilient element is attached relative to an adjacent vertebra. The end portion can be attached to the resilient portion to provide a stabilization construct that is movable in response to at least spinal extension, spinal flexion and lateral bending of the spinal column. The resilient portion, or bumper assembly, defines multiple planes and locations of motion relative to the longitudinal axis of the resilient element while providing appropriate stiffness and resistance for spinal stabilization as the spinal motion segment deviates from the neutral position and the bone anchor assemblies move closer together.

The anchor assemblies discussed herein can be multi-axial or uni-axial in form, and include an anchor member engageable to a vertebral body and a receiver, post or other device for receiving, connecting, or engaging the end portion or the resilient portion of the resilient element. The multi-axial anchor assemblies allow the anchor member to be positioned at various angles relative to the end portion of the anchor assembly. The uni-axial anchor assemblies can provide a fixed positioning of the end portion to the anchor member. The anchor member of the anchor assemblies can form a distal lower portion that is engageable to a vertebral body with the proximal resilient element connecting portion positioned adjacent the vertebral body.

The first and the second anchor assemblies can be the same or different. The first anchor assembly is configured to attach or connect to the end portion. The second anchor assembly is configured to provide an articulation surface to cooperate with the resilient portion.

In one embodiment, the first and/or second anchor assembly is in the form of a bone screw with a threaded shaft and a proximal head that is pivotally attached thereto, such as a pedicle screw. In other embodiments, the anchor member can be in the form of a hook, staple, cable, tether, suture anchor, interbody fusion implant, artificial disc implant, bolt, or other structure engageable to bony tissue. The resilient element connecting portion can include a receiver with a U-shape, O-shape, or other shape that defines a passage that receives the end member therein, thereon, therethrough, or thereover, for example.

In one embodiment the second anchor assembly includes a head, post, or other structure to provide an articulation surface for engagement with the resilient portion of the resilient element. The second anchor assembly can be provided with a structure, such as a projection, bump, irregularity, or the like to engage a corresponding indentation or groove in the resilient portion.

FIG. 1 illustrates one embodiment of a bone anchor-based dynamic stabilization system 10 in accordance with the present invention. A resilient element 12 includes an end portion 14 and a resilient portion 16. The end portion 14 is attachable with a first bone anchor assembly 18. The resilient portion 16 is engageable with a second bone anchor assembly 20.

Figure 2:
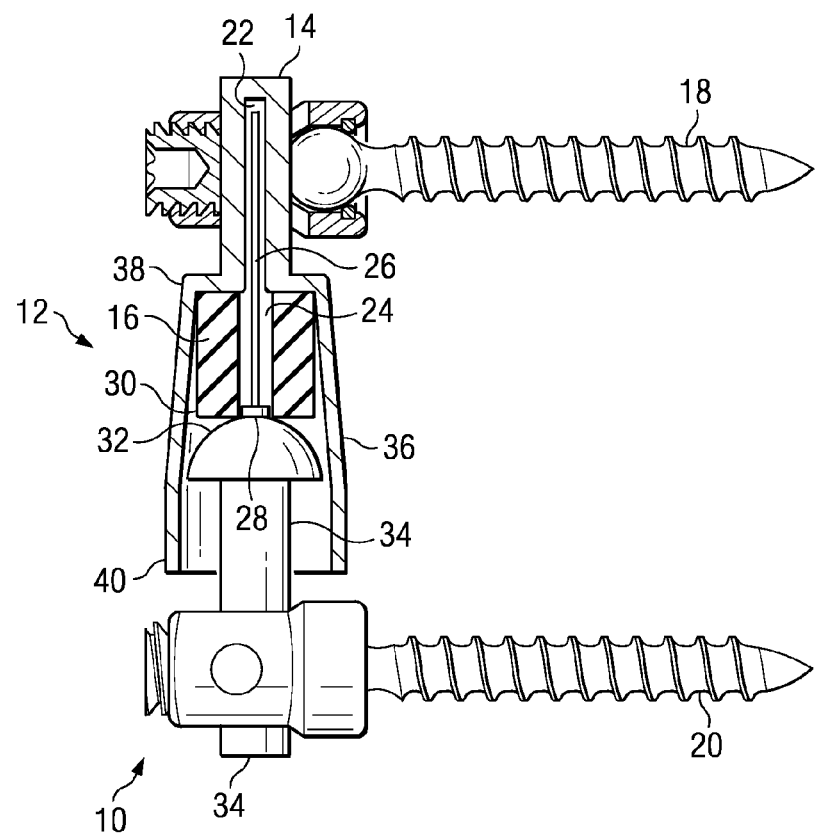
FIG. 2 is an elevational view, partially in cross section, of an embodiment of the present invention.

Resilient portion 16 and end portion 14 are attached or connected together. As illustrated in FIG. 2, in one embodiment, end portion 14 includes a first passage 22 at least partially therethrough and resilient portion 16 includes a second passage 24 at least partially therethrough. A tether 26 is disposed within the passages 22, 24 to connect the end portion 14 and the resilient portion 16. In one embodiment, the tether 26 is provided with a head, ferrule, or stop member 28 disposed outside of the resilient portion 16 and configured to retain the resilient portion 16 against the end portion 14.

In one embodiment, tether 26 is crimped within the first passage 22 to retain tether 26 in position. Various embodiments of crimping and disposition of the tether 26 within the passages 22, 24 are described in U.S. Ser. No. 11/028,999, filed Jan. 4, 2005, which is incorporated herein by reference in its entirety.

Other embodiments include end portion 14 and resilient portion 16 attached or connected together by other mechanical connections, such as clips, straps, or the like, or by adhesive, glue, epoxy, or the like, or by chemical bonding.

The cross-sectional shape of the resilient portion 16 may be circular, oval, or polygonal without departing from the spirit and scope of the invention. It is preferable, but not necessary, for the cross-sectional shape of the resilient portion 16 at the point of contact with the end portion 14 to match the cross-sectional shape of the end portion 14 at the point of contact with the resilient portion 16. The cross-sectional shape of the resilient portion 16 may vary along its length. The shape of the resilient portion 16 at its distal end 30 is selected to cooperate with an articulation surface 32 of the second bone anchor assembly 20. In one embodiment, this is the shape of a cup that cooperates with a corresponding shape of the articulation surface 32. Other embodiments include other shapes for the resilient portion 16, the distal end 30, and articulation surface 32 without departing from the spirit and scope of the invention. For example, the resilient portion 16 may be configured to partially surround a post-like structure, head, etc., 34 associated with the second bone anchor assembly 20. Such a post-like structure 34 is illustrated in FIG. 2. The distal end 30 is substantially flat in some embodiments, such as illustrated in FIGS. 1 and 2.

The articulation surface 32 of the second bone anchor assembly 20 may be attached to and, thus, part of the bone anchor assembly 20 and not integral to other portions of the bone anchor assembly 20. Or the articulation surface 32 of the second bone anchor assembly 20 may be integral thereto.

The system 10 also includes a sheath 36 having a proximal end 38 connected to the end portion 14 and a distal end 40 at least partially circumferentially surrounding and spaced from the articulation surface 32. The sheath 36 is designed such that it will at least partially circumferentially surround the articulation surface 32 when the resilient portion 16 and the articulation surface 32 are separated by a pre-determined distance, to be discussed in greater detail below.

The proximal end 38 is connected to and part of the end portion 14 by any conventional means and in some embodiments is integral with the end portion 14. The cross-sectional shape of the proximal end 38 and the distal end 40 may be the same or different and may be selected without departing from the spirit and scope of the invention. In one embodiment, the cross-sectional shape of the distal end 40 is designed to cooperate with the post-like structure 34 and the articulation surface 32 to minimize any resistance from engagement of the post-like structure 34 or the articulation surface 32 with the sheath 36 as the resilient element 12 and the post-like structure 34 are moved away from each other.

In some embodiments, the sheath 36 is not connected to the second bone anchor assembly 20 or any part thereof. In other embodiments, described in more detail below, the sheath 36 is connected to the bone anchor assembly 20. In some embodiments, the sheath 36 is inflexible or substantially inflexible. In other embodiments, the sheath 36 is flexible or substantially flexible. In some embodiments, the sheath 36 is open at the distal end 40.

As illustrated in FIG. 1, some embodiments include a protrusion 42 on the resilient portion 16. This protrusion mates with the sheath 36 for fixing the resilient portion 16 to the sheath 36.

Figure 3:
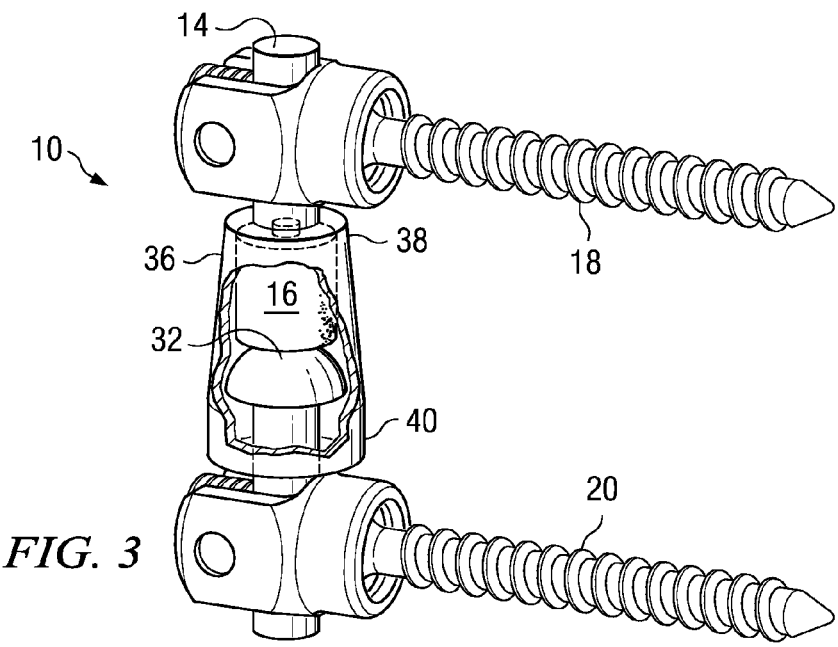
FIG. 3 is a perspective view, with a partial cutaway, of an embodiment of the present invention.

FIG. 3 illustrates the sheath 36 having a cup shape and at least partially circumferentially surrounding and spaced apart from the articulation surface 32.

Figure 4:
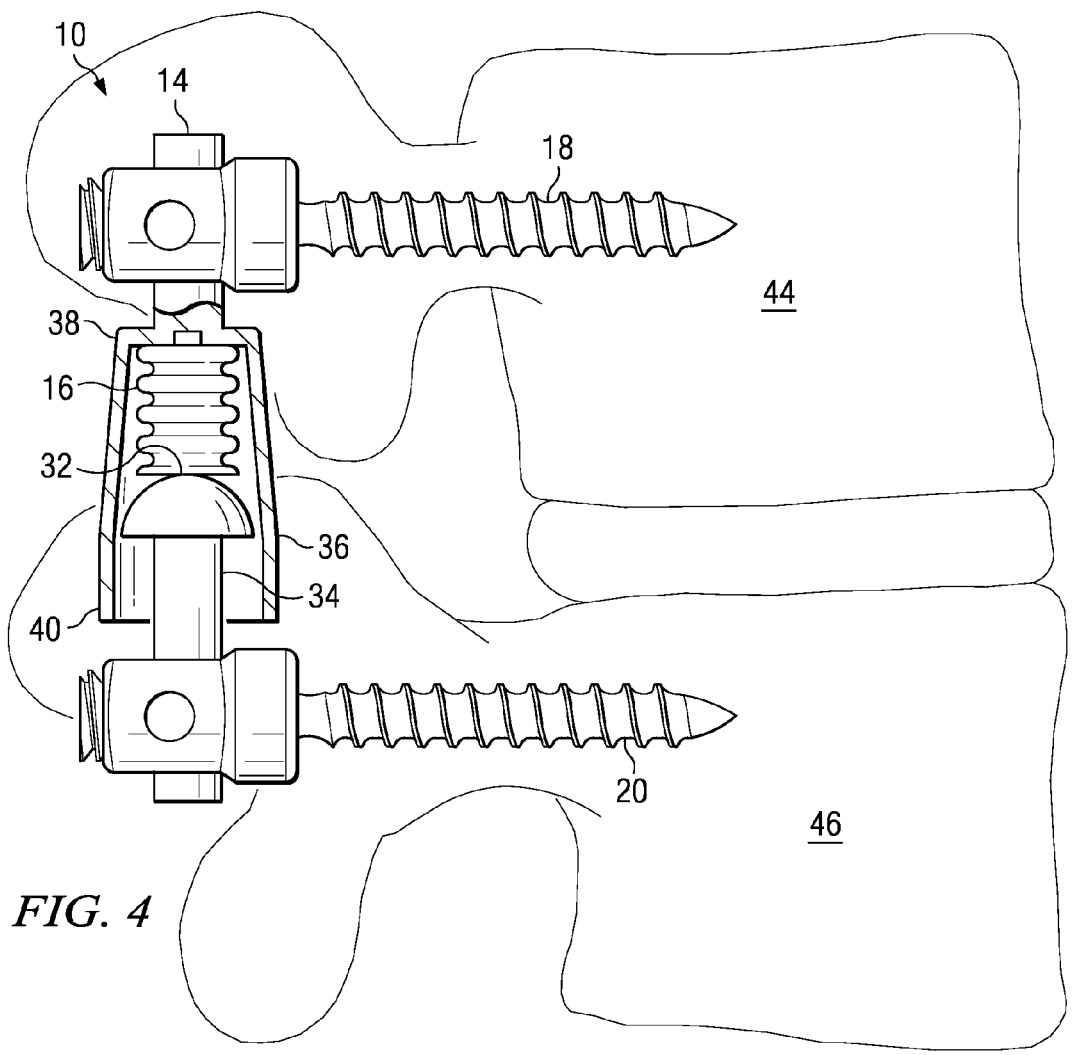
FIG. 4 is an elevational view, partially in cross section, of an embodiment of the present invention.

FIG. 4 illustrates a resilient portion 16 having a corrugated shape. This may provide more flexibility to the resilient portion 16.

Figure 5:
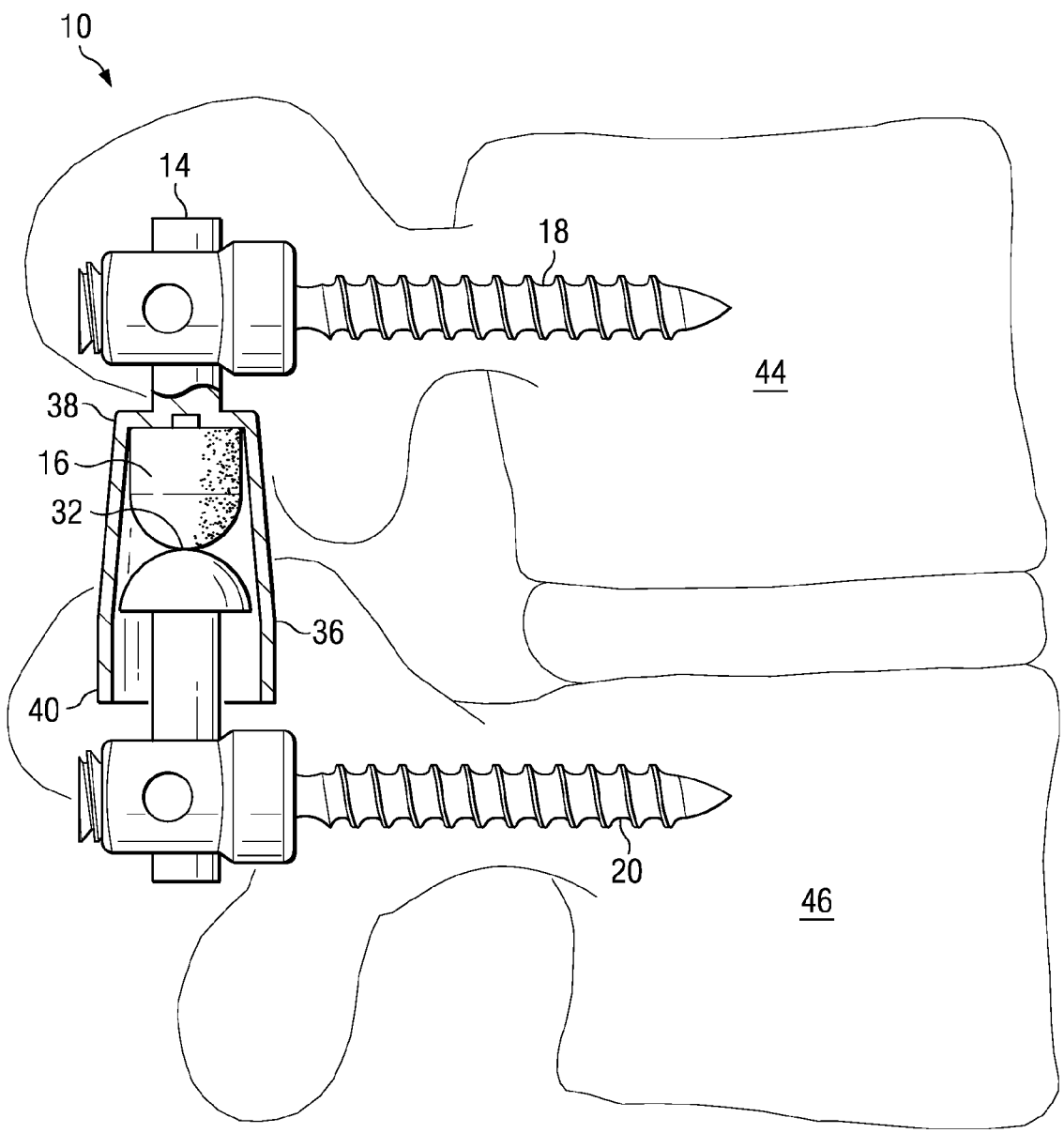
FIG. 5 is an elevational view, partially in cross section, of an embodiment of the present invention.

FIG. 5 illustrates the resilient portion 16 having a rounded shape that may provide different flexibility characteristics.

The shape of the resilient portion 16 may be selected without departing from the spirit and scope of the invention to provide selected flexibility, ease of manufacturing, etc. The material of construction of the resilient portion 16 may also be selected without departing from the spirit and scope of the invention. Some suitable materials are included in U.S. Ser. No. 11/028,999, which is incorporated herein by reference in its entirety.

Figure 6:
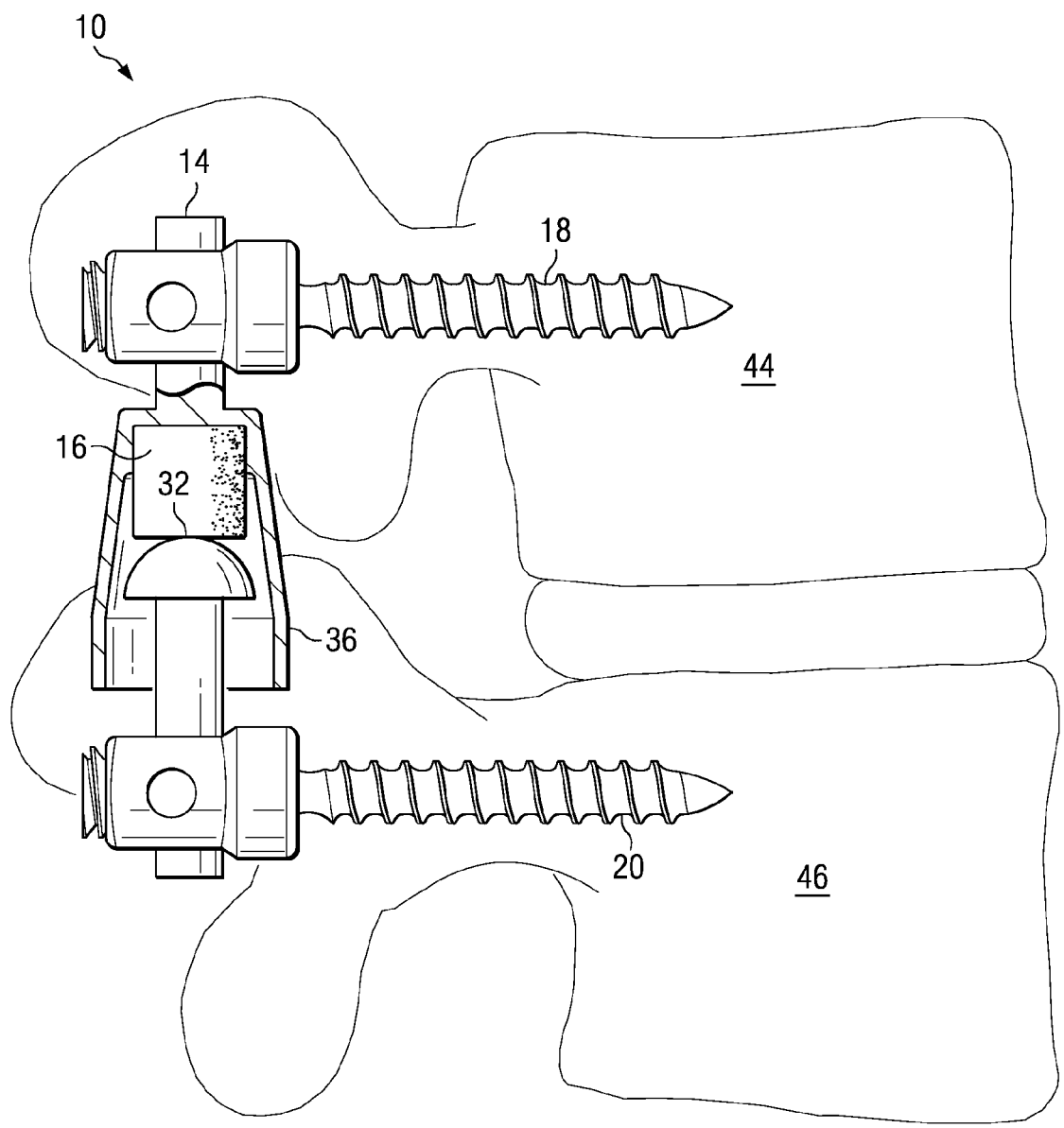
FIG. 6 is an elevational view, partially in cross section, of an embodiment of the present invention.

FIG. 6 illustrates another embodiment of the present invention in which the resilient portion 16 is at least partially circumferentially surrounded by the sheath 36. In this embodiment, the resilient portion 16 is embedded into the sheath 36 by more than the protrusion 42 illustrated in FIG. 1. Again, the resilient portion 16 may be engaged to or fixed with the sheath 36 in any conventional manner, as discussed above.

FIG. 6 also illustrates the system 10 affixed to a first substrate 44 and a second substrate 46. The system 10 is illustrated in a neutral position. As illustrated in FIG. 6, the resilient portion 16 and the articulation surface 32 are touching, and the resilient portion 16 is uncompressed, when the system 10 is in a neutral position. In other embodiments, the resilient portion 16 and the articulation surface 32 are not touching in the neutral position. In other embodiments, the resilient portion 16 is compressed in the neutral position. In some embodiments, the first bone anchor assembly 18 is affixed to the first substrate 44 and the second bone anchor assembly 20 is affixed to the second substrate 46.

The substrates 44, 46 are living human vertebrae when the system 10 is used in a living human surgical procedure. In other embodiments, the substrates 44, 46 may be cadaveric human vertebrae, living or non-living animal vertebrae, sawbones, artificial bone, plastic, vertebral replicas, blocks, or any living or non-living vertebrae without departing from the spirit and scope of the invention. For example, the system 10 may be used for training purposes, demonstration purposes, development and testing purposes, etc., without being used for a surgical procedure on a living human.

Figure 7:
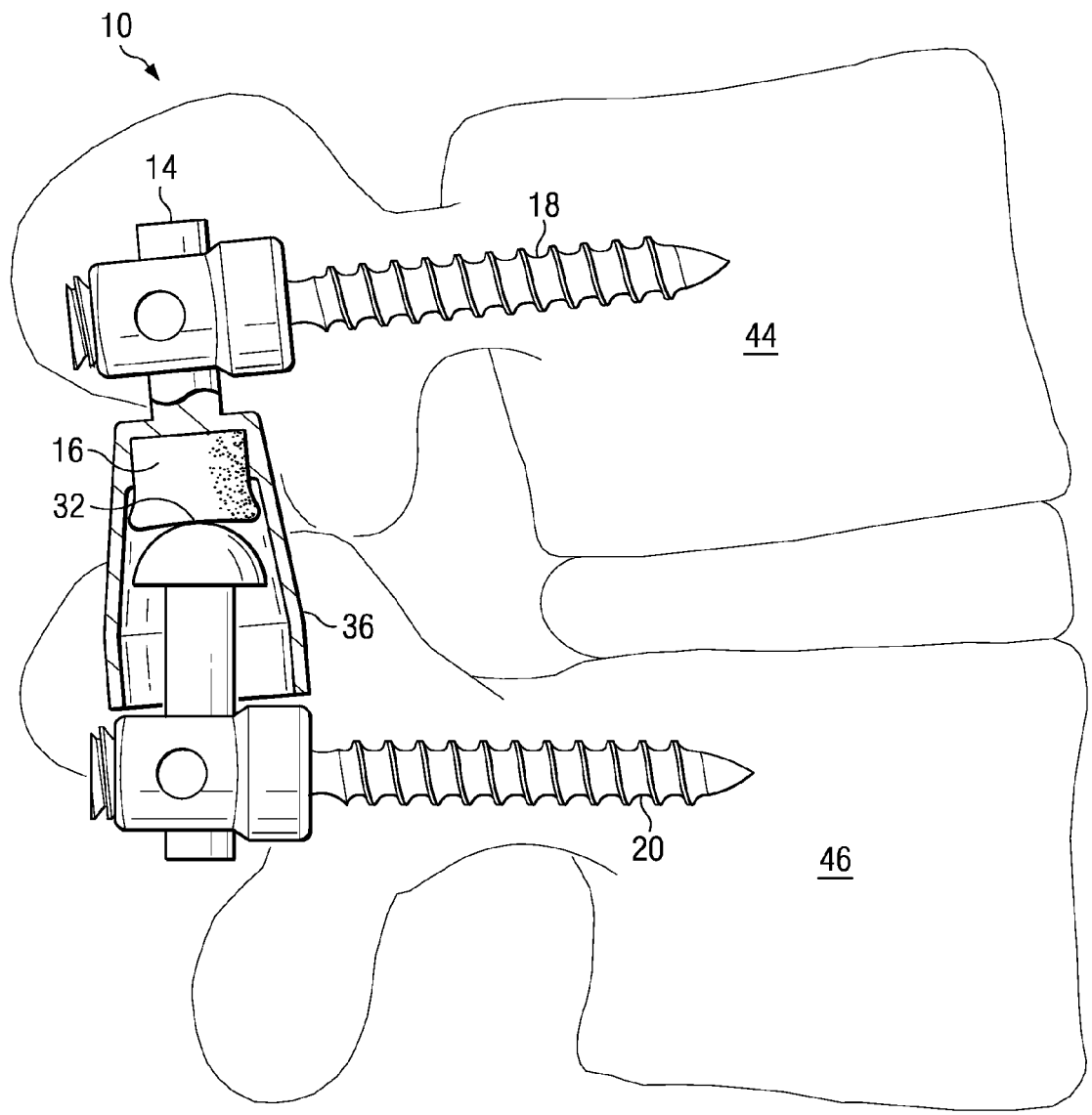
FIG. 7 is an elevational view, partially in cross section, of an embodiment of the present invention in an extension position.

FIG. 7 illustrates the system 10 in which the substrates 44, 46 or bone anchor assemblies 18, 20 are moved toward each other and the resilient portion 16 deforms into a compressed state, resiliently resisting the movement of the first bone anchor assembly 18 and the second bone anchor assembly 20 towards each other. This would occur, for example, during extension of the spine, moving the vertebrae and the bone anchor assemblies 18, 20 toward each other.

Figure 8:
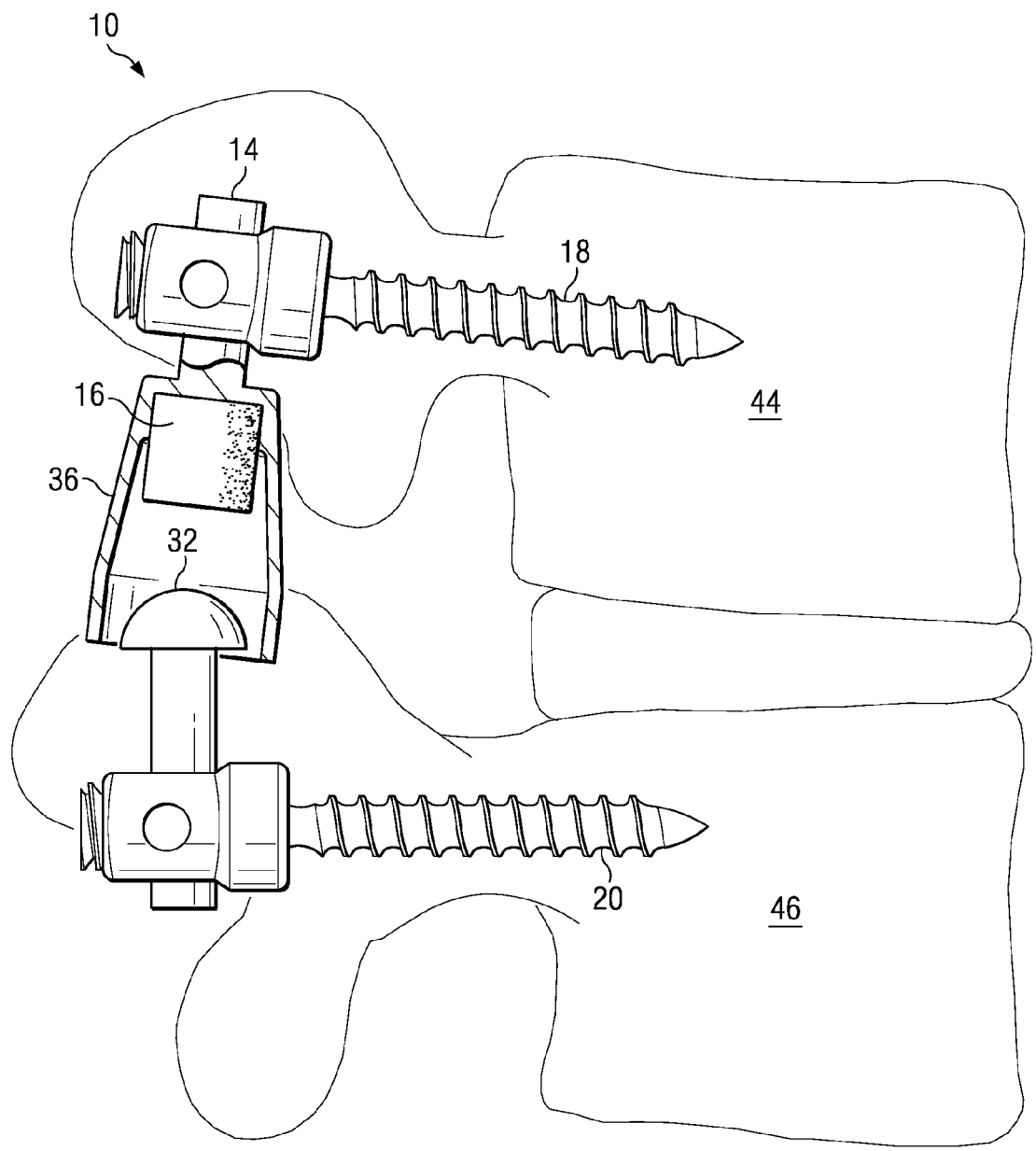
FIG. 8 is an elevational view, partially in cross section, of an embodiment of the present invention in a flexion position.

FIG. 8 illustrates the system 10 in which the substrates 44, 46 or bone anchor assemblies 18, 20 are moved away from each other and the resilient portion 16 and the articulation surface 32 are not engaged. This would occur, for example, during flexion of the spine, moving the bone anchor assemblies 18, 20 away from each other. FIGS. 7 and 8 illustrate that the resilient portion 16 and the articulation surface 32 are engageable and separable, thus separably engageable.

The sheath 36 prevents significant lateral movement of resilient element 12 and articulation surface 32 relative to each other. This allows the resilient portion 16 and the articulation surface 32 to be engageable when the bone anchor assemblies 18, 20 are again moved toward each other.

Figure 9:
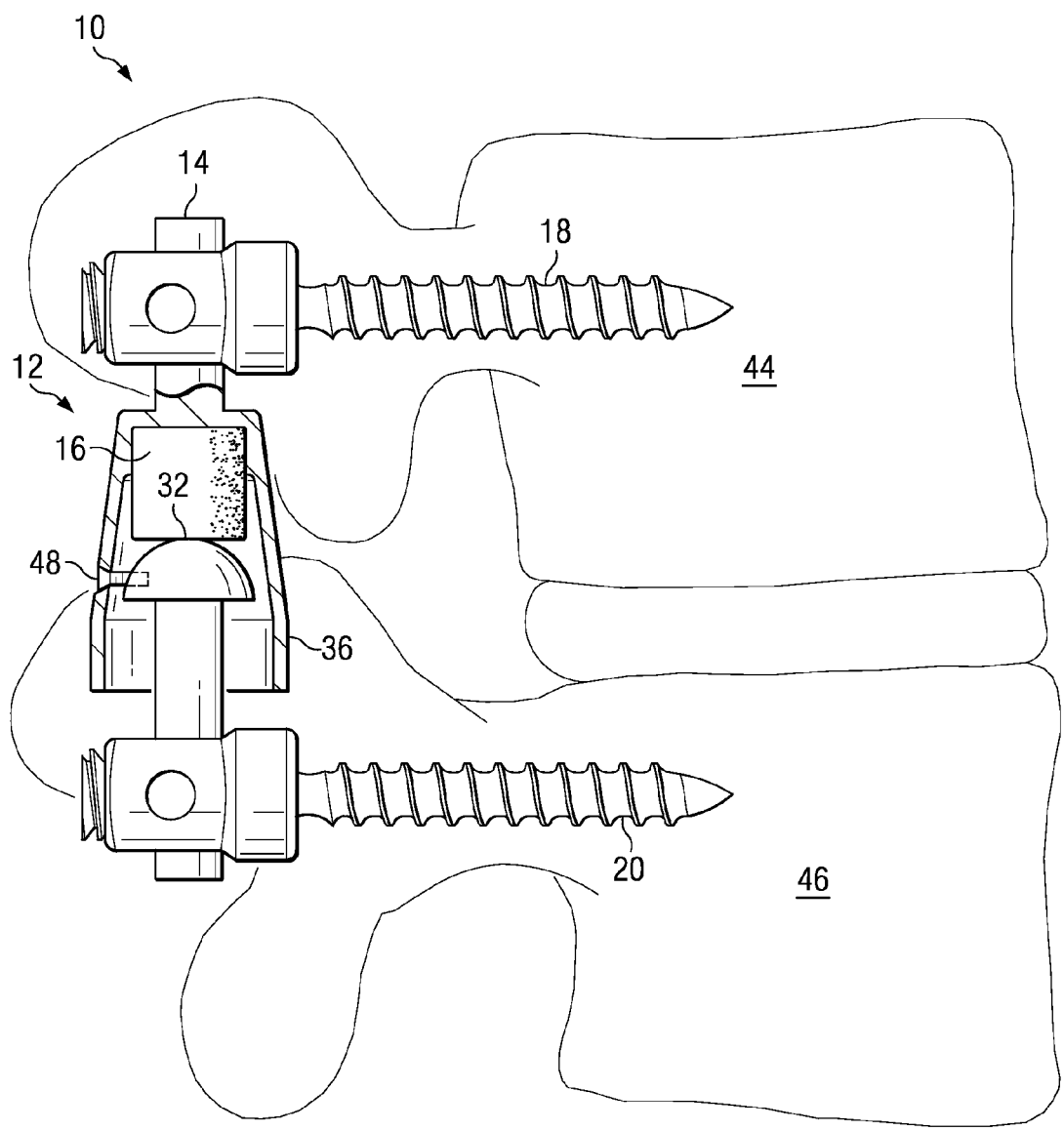
FIG. 9 is an elevational view, partially in cross section, of an embodiment of the present invention.

FIG. 9 illustrates a set screw 48 that is enagagable with both the resilient element 12 and the second bone anchor assembly 20. This set screw serves to fix the resilient element 12 and the second bone anchor assembly 20 to convert the system to a rigid or semi-rigid system. In this state, there will be limited movement of the resilient element 12 and the second bone anchor assembly 20 relative to each other to provide greater fixated stabilization to the substrates 44, 46. This could be used, for example, for revision surgery if it is desired to revise the system 10 to fix adjacent vertebrae relative to each other.

Figure 10:
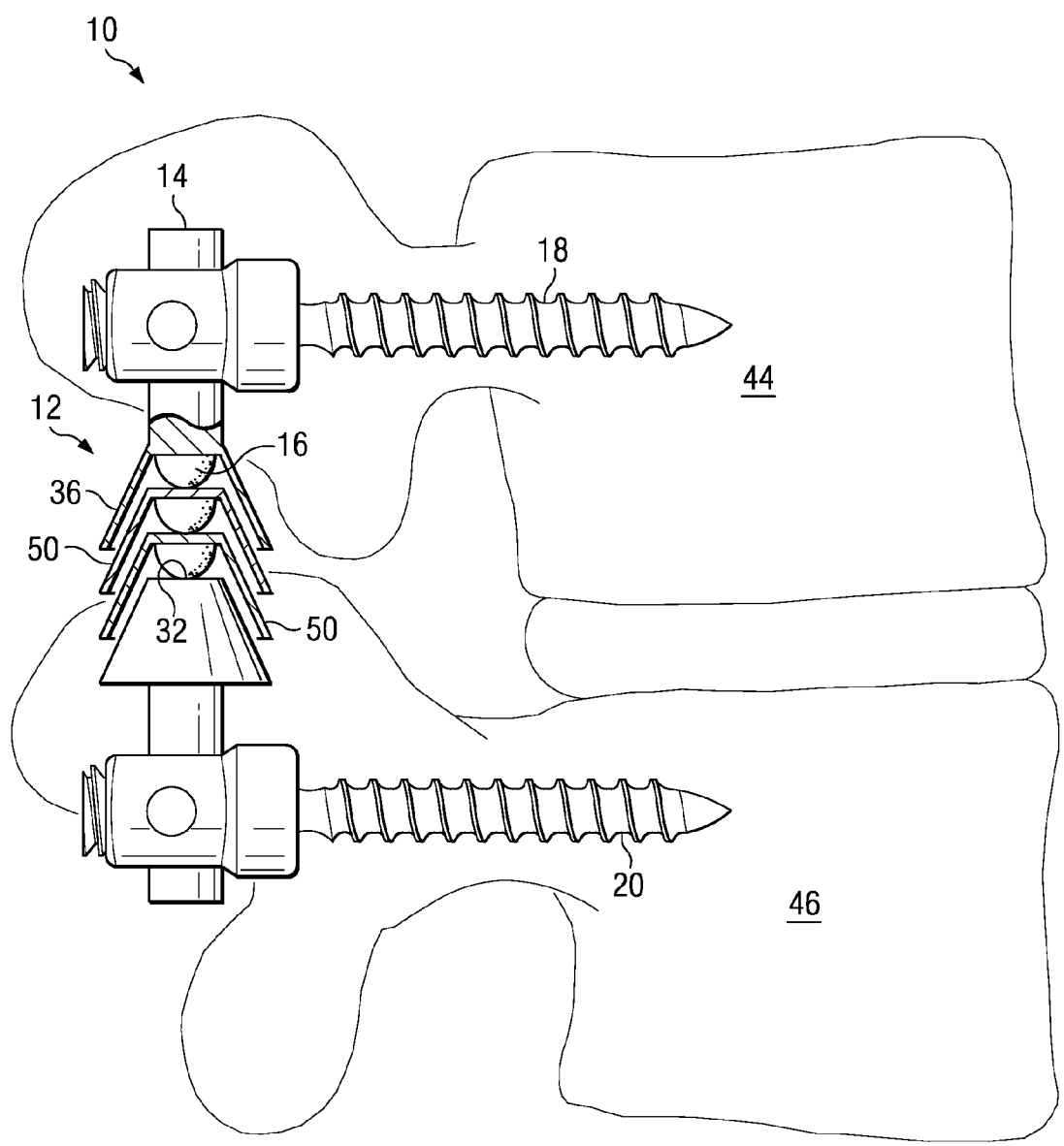
FIG. 10 is an elevational view, partially in cross section, of an embodiment of the present invention.
Figure 11:
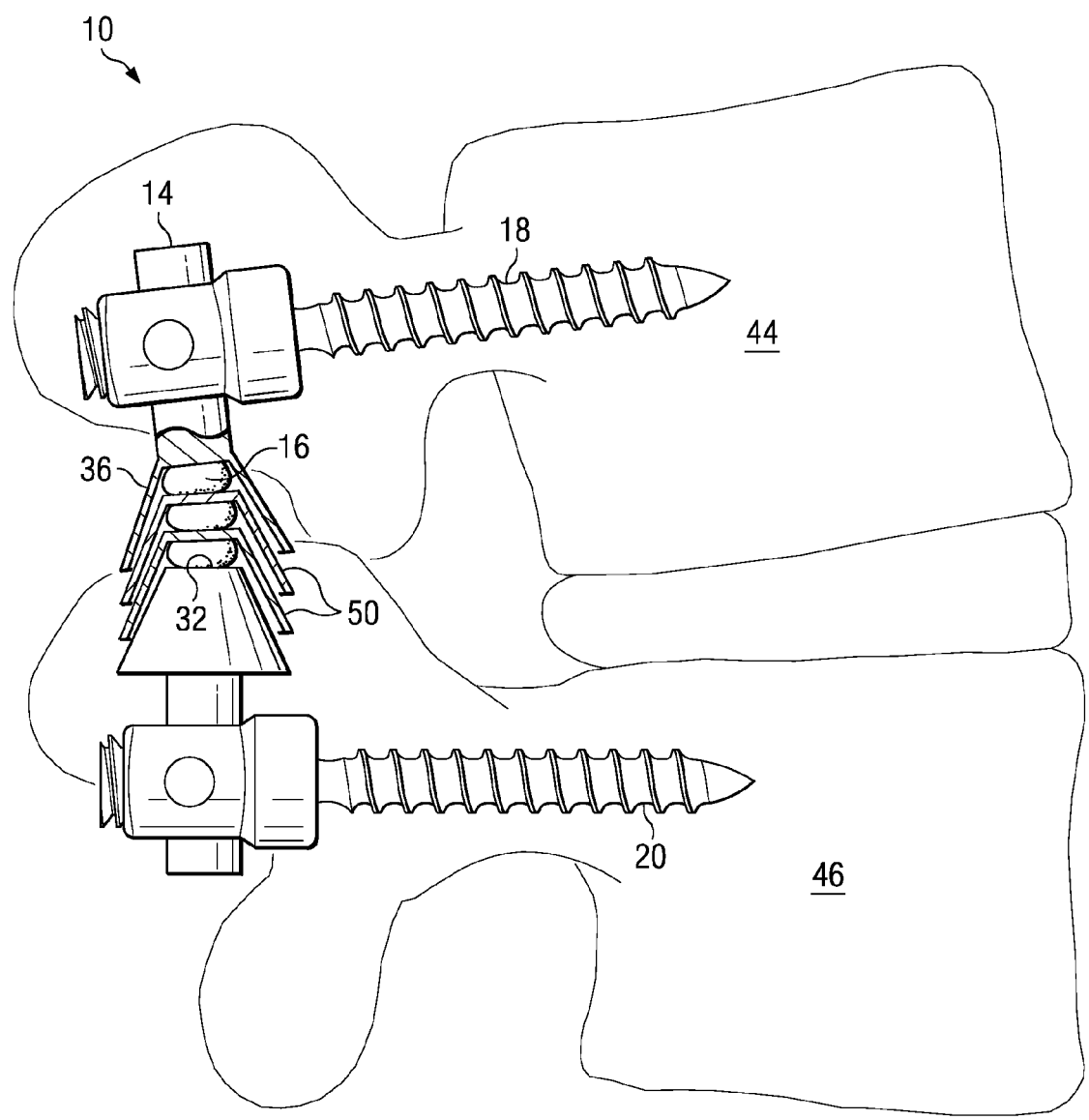
FIG. 11 is an elevational view, partially in cross section, of an embodiment of the present invention in an extension position.
Figure 12:
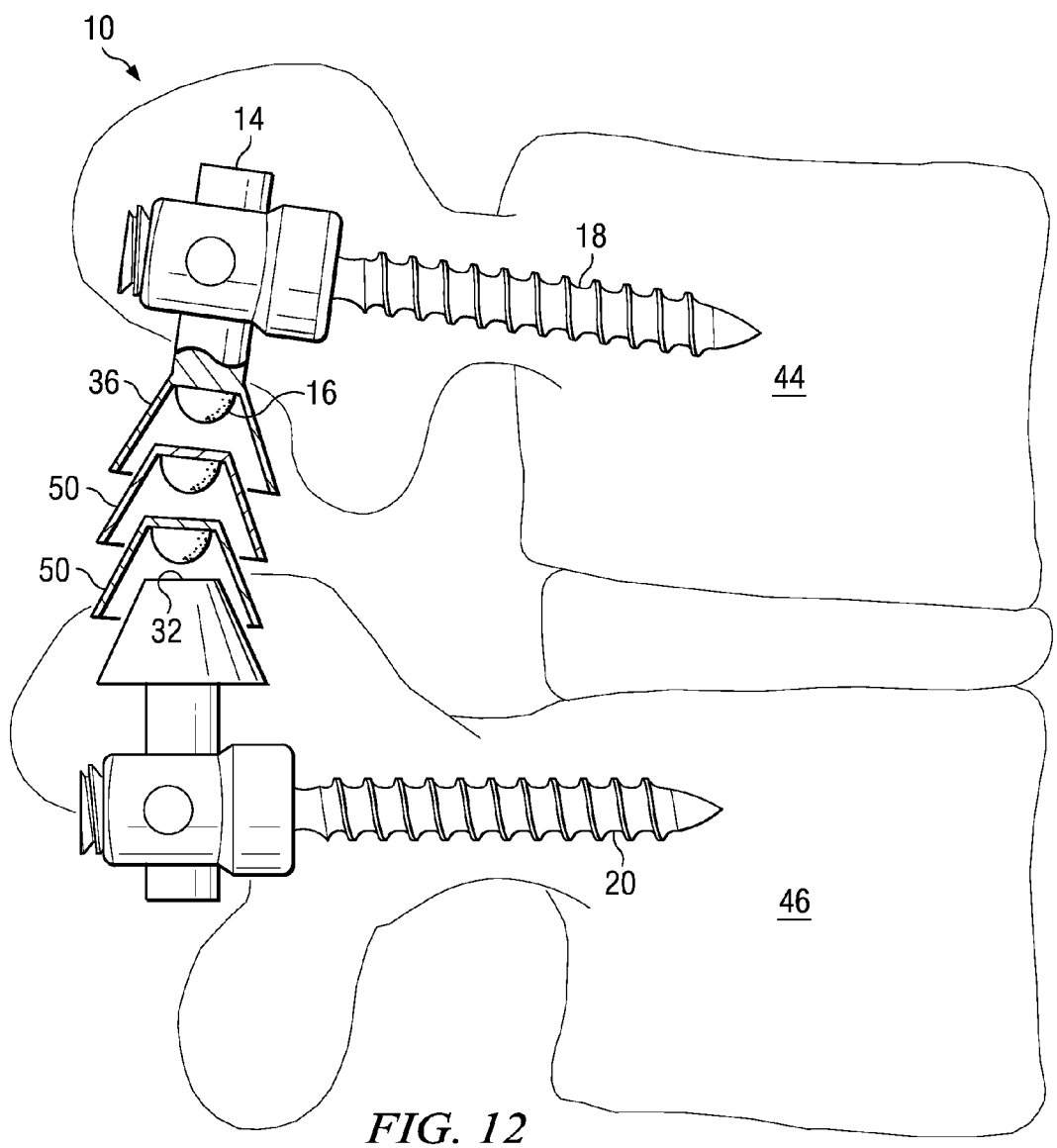
FIG. 12 is an elevational view, partially in cross section, of an embodiment of the present invention in a flexion position.

FIGS. 10-12 illustrate embodiments in which the resilient element 12 includes a plurality of resilient portions 16 and a plurality of sheaths 36. Each sheath or cup portion 36 has an associated resilient portion 16 and together is an intermediate resilient element 50. The intermediate resilient elements 50 are nested or arranged such that one sheath 36 fits within at least one adjacent sheath 36. A resilient portion 16 is disposed between each sheath 36. Each intermediate resilient element 50 is separably engageable with at least one other intermediate resilient element 50, the articulation surface 32, or the resilient element 12.

The resilient portions 16 are engaged with the sheaths 36 in each intermediate resilient element 50 similarly to that described above for the resilient element 12. The individual resilient portions 16 in the intermediate resilient elements 50 may be the same shape, material, etc., or may be different shapes, materials, etc., without departing from the spirit and scope of the invention.

FIG. 10 illustrates the system 10 with a plurality of intermediate resilient elements in a neutral state. FIG. 11 illustrates the system 10 with a plurality of intermediate resilient elements 50 in an extension position, in which the bone anchor assemblies 18, 20 are moved closer together. When this occurs, the resilient portions 16 are compressed, similarly to that described above. FIG. 12 illustrates the system 10 with a plurality of intermediate resilient elements 50 in the flexion position, in which the bone anchor assemblies 18, 20 are moved away from each other. When this occurs, the resilient portions 16 are disengaged from the adjacent intermediate resilient portion 50 and from the articulation surface 32, similarly to that described above.

One of ordinary skill in the art will be able to determine variations in the size, shape, materials, and other parameters for the plurality of intermediate resilient elements 50 and the resilient portions 16 therein to accomplish desired results relating to compressability, allowable extension or compression distances, lateral displacement, shear resistances, and other parameters.

Figure 13:
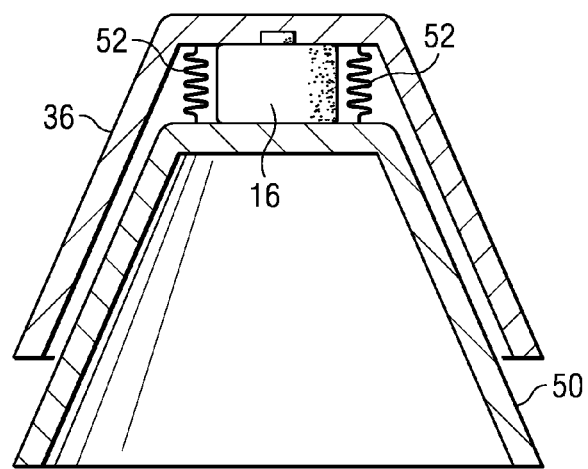
FIG. 13 is an elevational cross section view of an embodiment of a sheath in accordance with the present invention.

FIG. 13 illustrates an embodiment in which adjacent intermediate resilient elements 50 are attached to each other with a connector 52. The connector 52 prevents complete decoupling of the adjacent intermediate resilient elements 50 during excessive flexion conditions, when the bone anchor assemblies are moved apart a predetermined distance. Again, one of ordinary skill in the art will be able to determine without undue experimentation the parameters, materials, etc., associated with the connector 52 to accomplish the specific performance for a specific situation without departing from the spirit and scope of the invention. The connector 52 may be made from any material and may be resilient, flexible, folded, convoluted, spring-like, etc. The connector 52 may assert a force against the adjacent intermediate resilient elements 50, such as a pre-loaded disposition of adjacent intermediate resilient elements 50 away from each other to provide a distraction force upon adjacent vertebrae.

Figure 14:
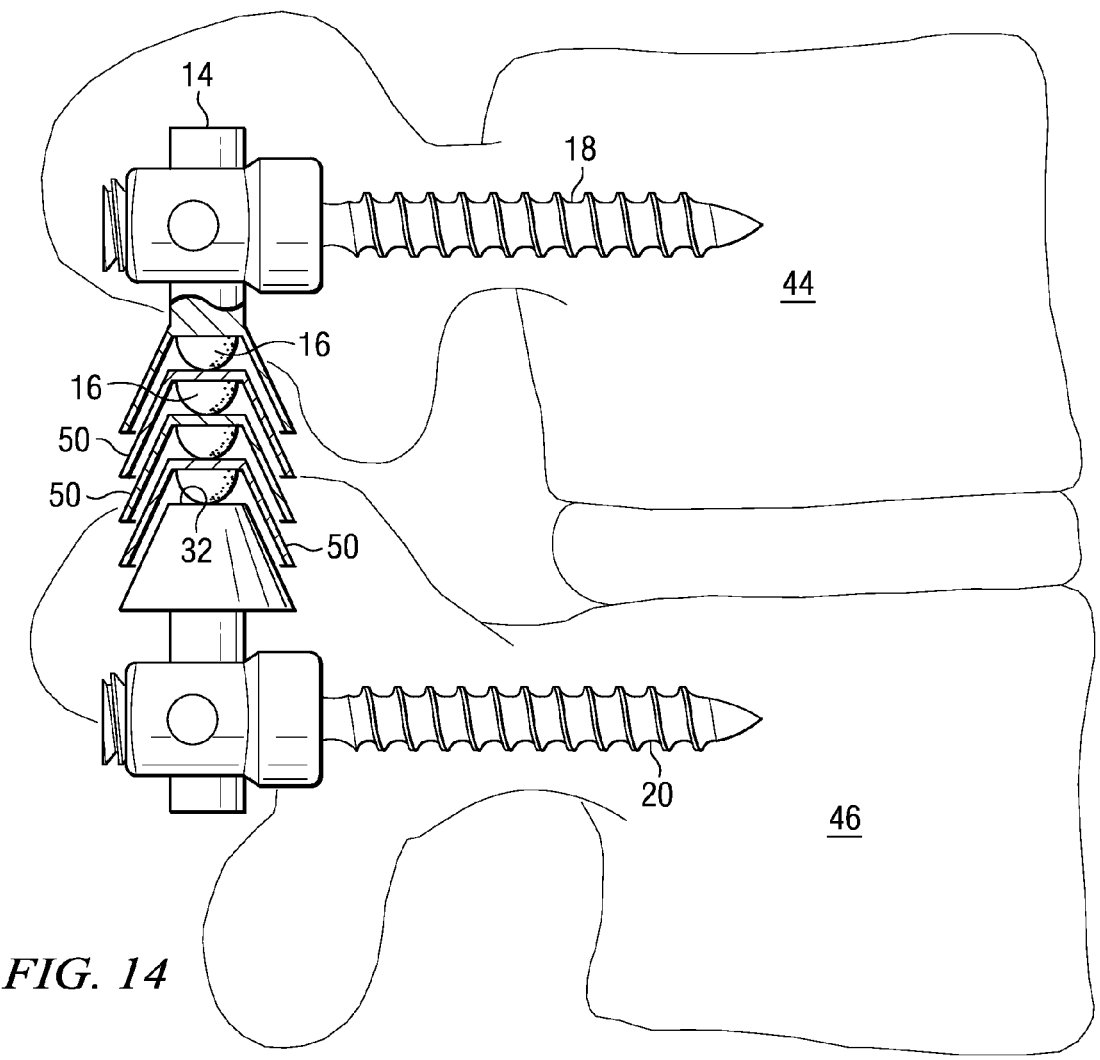
FIG. 14 is an elevational view, partially in cross section, of an embodiment of the present invention.

FIG. 14 illustrates an embodiment in which the resilient portions 16 of the intermediate resilient elements 50 are semispherical, or have at least one spherical surface. The articulation surface 32 in this embodiment is frustroconical shape.

Figure 15:
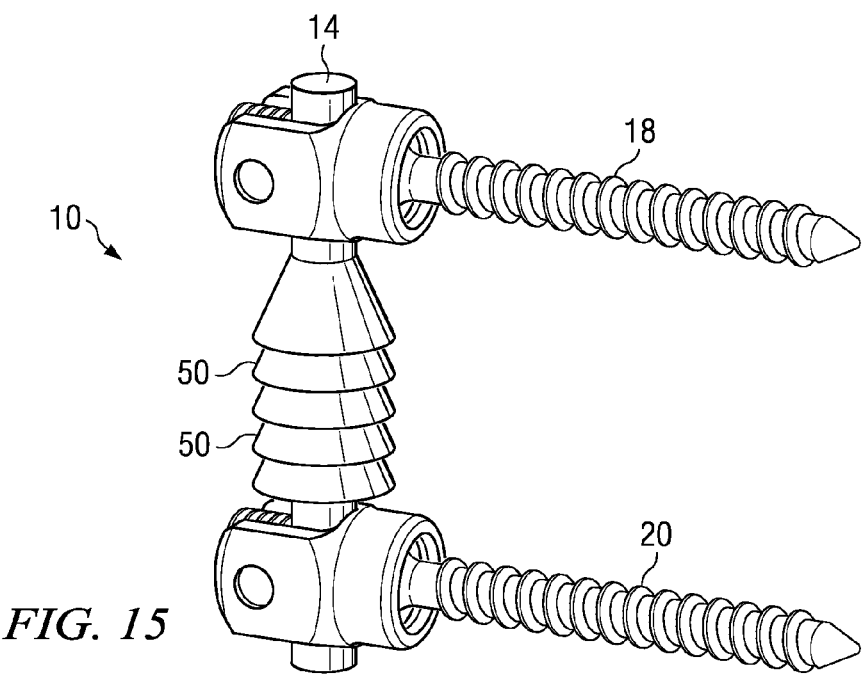
FIG. 15 is a perspective view of an embodiment of the present invention.

FIG. 15 illustrates an embodiment of the system 10 having a plurality of intermediate resilient elements 50 that is not engaged to substrates 44, 46.

Figure 16:
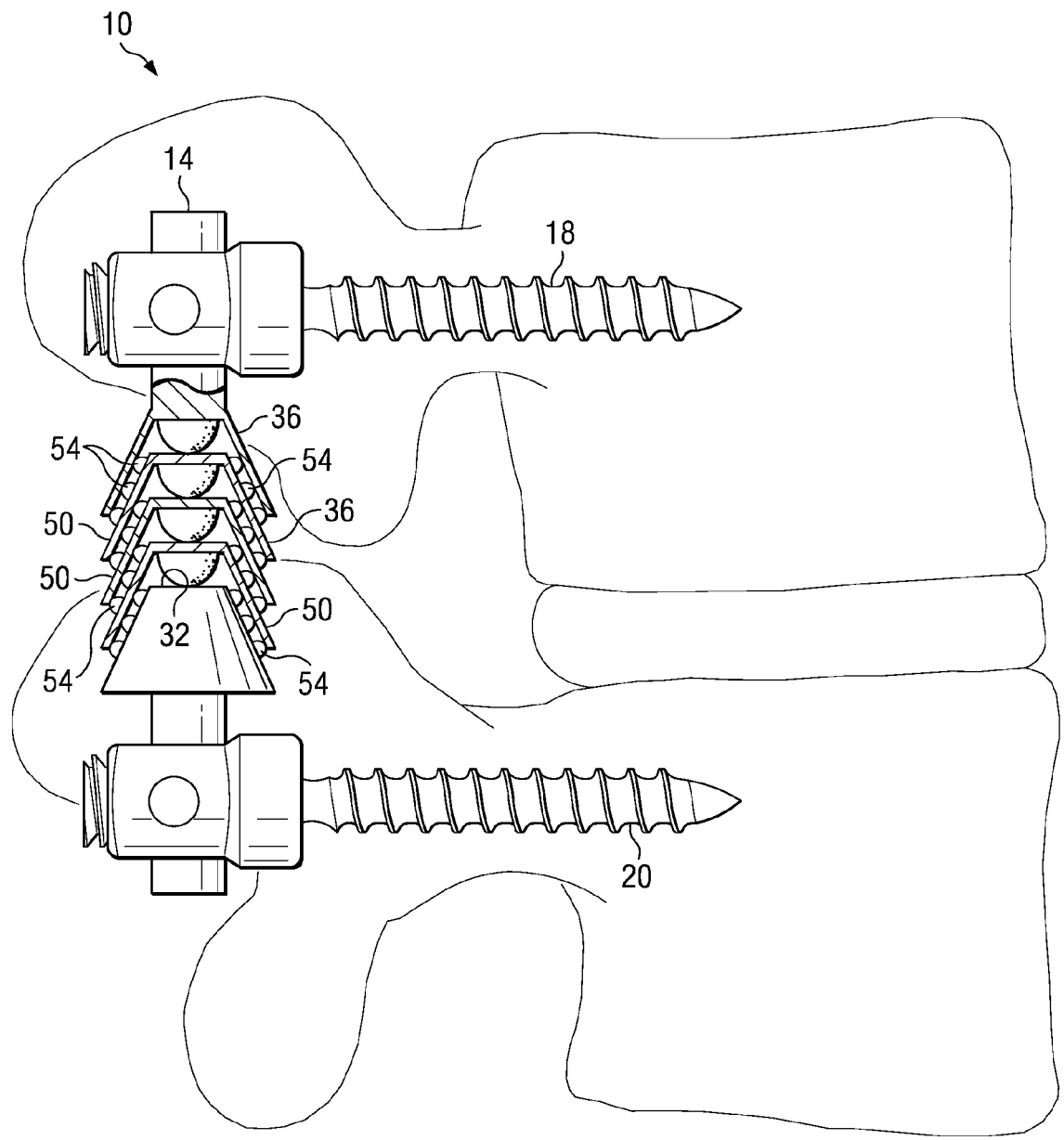
FIG. 16 is an elevational view, partially in cross section, of an embodiment of the present invention.

FIG. 16 illustrates an embodiment of the system 10 having a plurality of intermediate resilient elements 50 in which lateral bumpers 54 are present between the sheaths 36 of adjacent intermediate resilient elements 50. The lateral bumpers 54 may be attached to either an outer surface of the sheath 36 or an inner surface of the sheath 36. In the illustrated embodiment, the lateral bumpers are attached to the inner surface of the sheaths 36. The lateral bumpers 54 may be discrete bumpers spaced around the periphery of the sheath 36 or may be continuous about the periphery of the sheath 36. As illustrated in FIG. 16, there are three tiers of lateral bumpers 54 associated with each intermediate resilient element 50, but there may be any number of tiers, including one tier, of bumpers.

Figure 17:
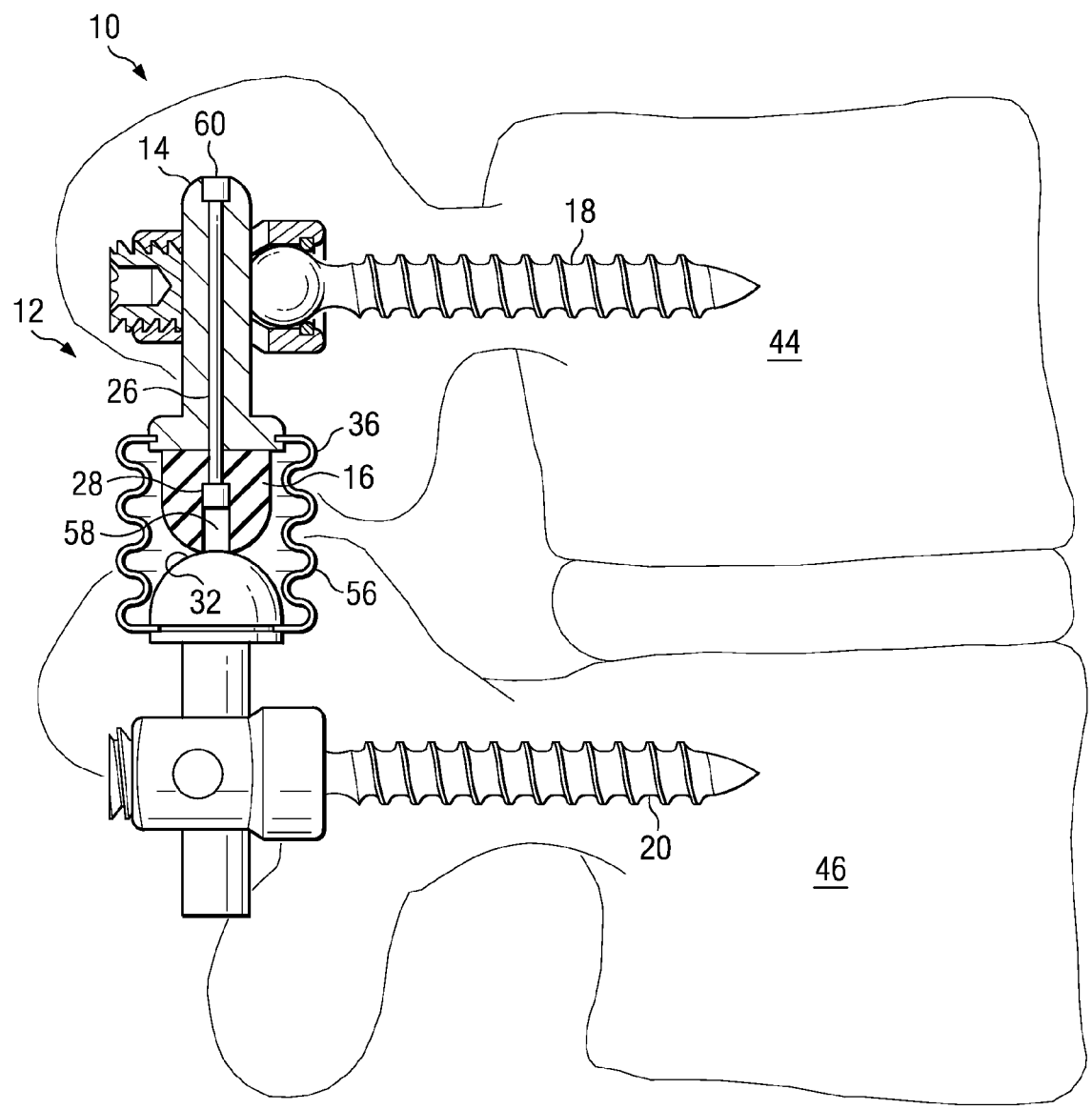
FIG. 17 is an elevational view, partially in cross section, of an embodiment of the present invention.

FIG. 17 illustrates an embodiment of the system 10 in which the sheath 36 is attached to both the resilient element 12 and the second bone anchor assembly 20. In this embodiment, the sheath 36 is a flexible expandable casing or bellows 56. The casing 56 surrounds the articulation surface 32 and the resilient portion 16.

Also illustrated in FIG. 17, the head 28 attached to the tether 26 is disposed within an indentation or cavity 58 in the resilient portion 16. An opposing head or stop 60 is attached to the opposite end of the tether 26 and disposed at the opposite end of the end portion 14. Thus, the tether 26 secures the resilient portion 16 to the end portion 14, similarly to the securing arrangement described above.

FIG. 17 illustrates this embodiment in a neutral position, in which the resilient portion 16 abuts the articulation surface 32 without compression of the resilient portion 16. Again, as discussed above, the resilient portion 16 may be compressed or not abutting the articulation surface 32 in the neutral position, depending on the specific arrangement and engineering parameters selected for a particular circumstance.

Figure 18:
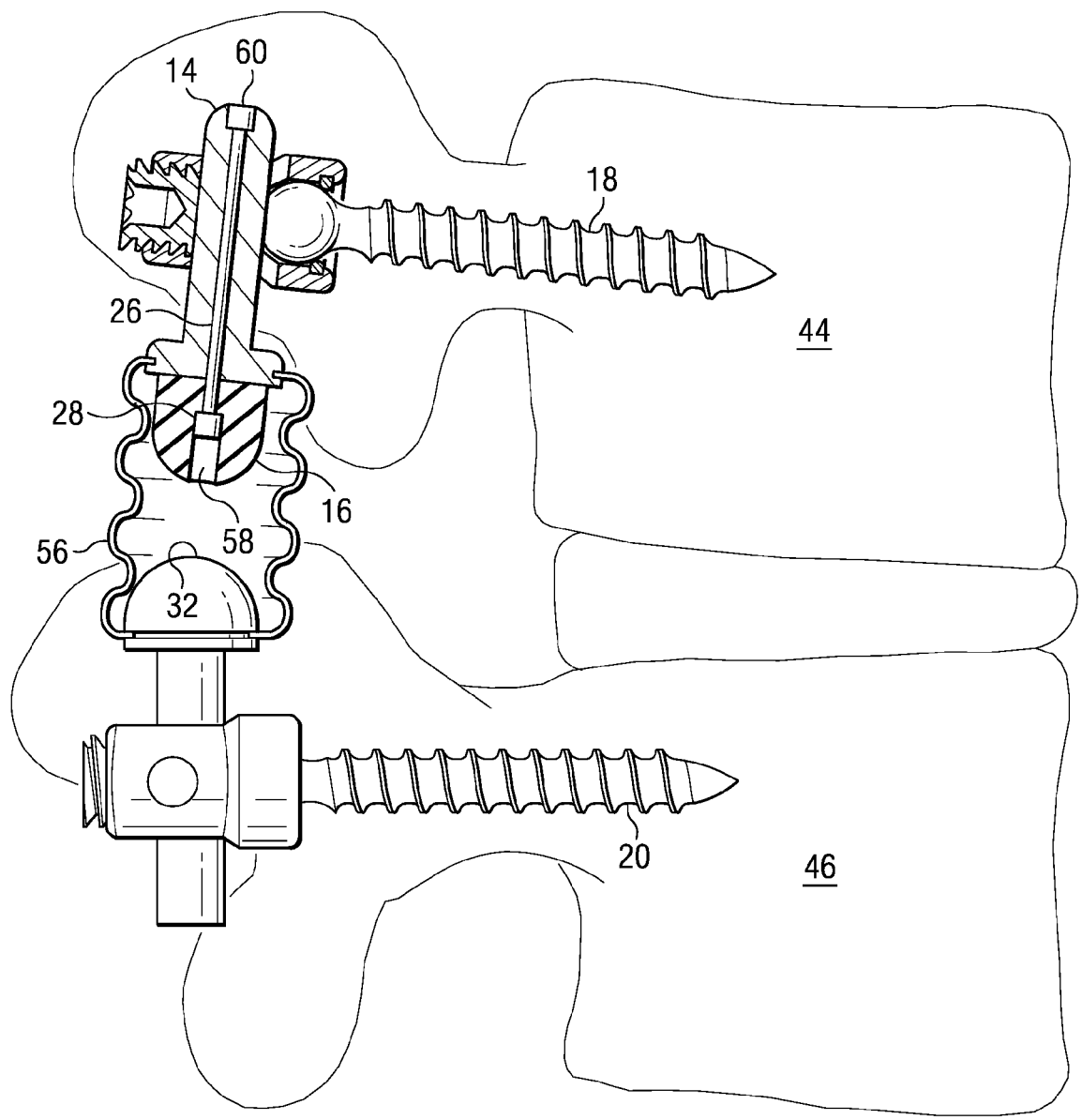
FIG. 18 is an elevational view, partially in cross section, of an embodiment of the present invention in a flexion position.

FIG. 18 illustrates this embodiment in the flexion position, in which the bone anchor assemblies 18, 20 are moved apart relative to the neutral position. The casing 56 presents little or minimal resistance to moving the bone anchor assemblies 18, 20 apart. The casing 56 is configured to expand as the bone anchor assemblies 18, 20 are moved apart, such that the casing 56 continues to surround the articulation surface 32 and the resilient portion 16.

Figure 19:
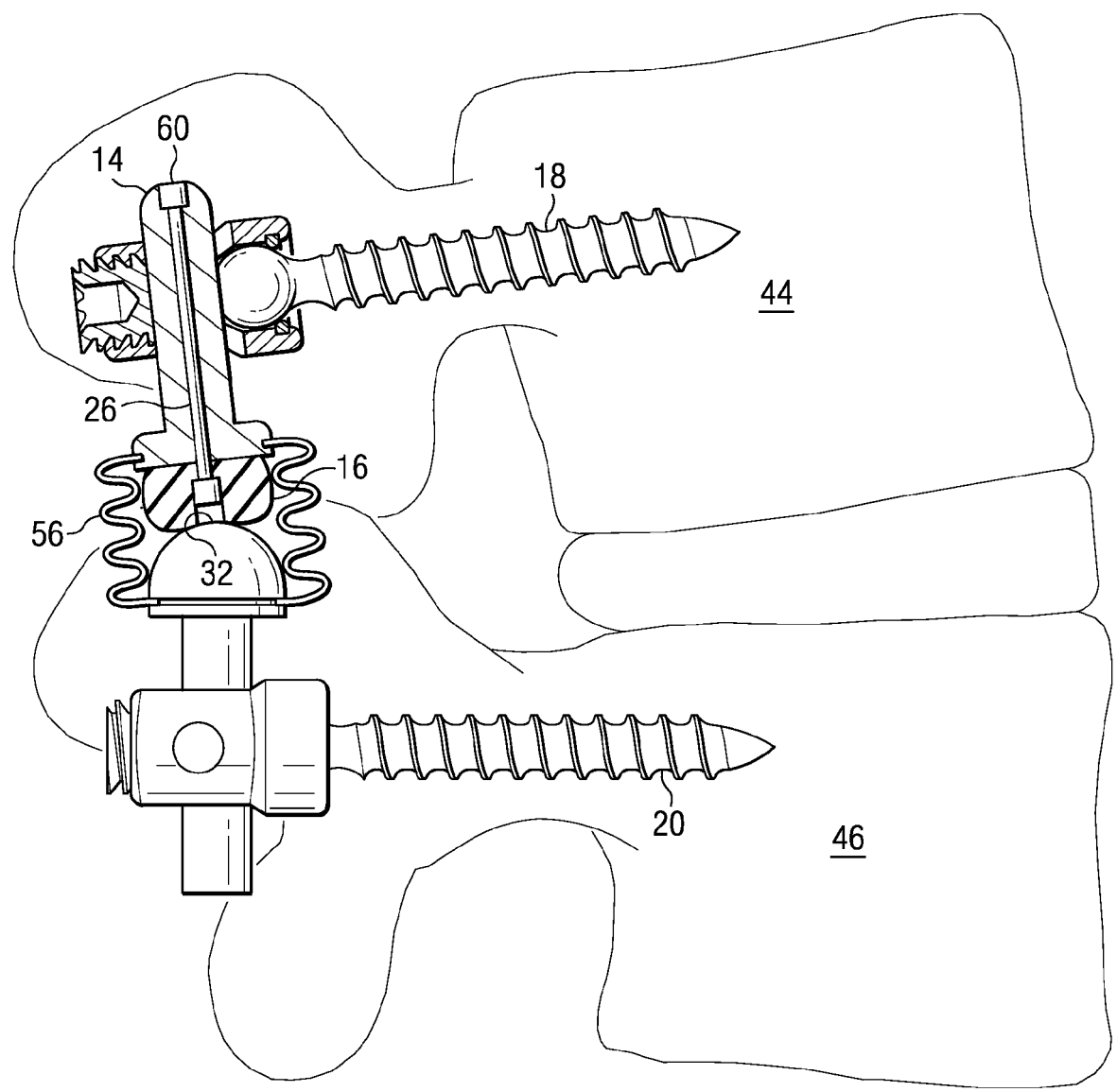
FIG. 19 is an elevational view, partially in cross section, of an embodiment of the present invention in an extension position.

FIG. 19 illustrates this embodiment in which the bone anchor assemblies 18, 20 are spaced closer together than in the neutral position and the resilient portion 16 is compressed. The casing 56 presents little or minimal resistance to moving the bone anchor assemblies 18, 20 closer together. The casing 56 is configured to collapse as the bone anchor assemblies 18, 20 are moved together, such that the casing 56 continues to surround the articulation surface 36 and the resilient portion 16.

The casing 56 may be constructed of any material and of any shape. The casing 56 may be porous to allow the exchange of fluid between the space within the casing 56 and external to the casing 56. Preferably the casing is constructed from a biocompatible material if the system 10 is to be affixed to a living substrate.

Figure 20:
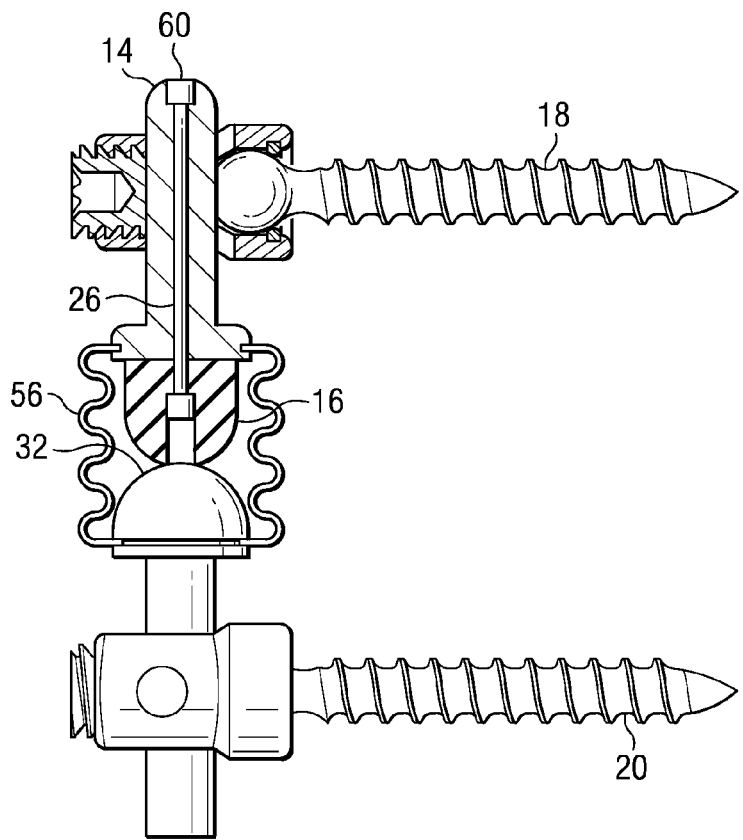
FIG. 20 is an elevational view, partially in cross section, of an embodiment of the present invention.
Figure 21:
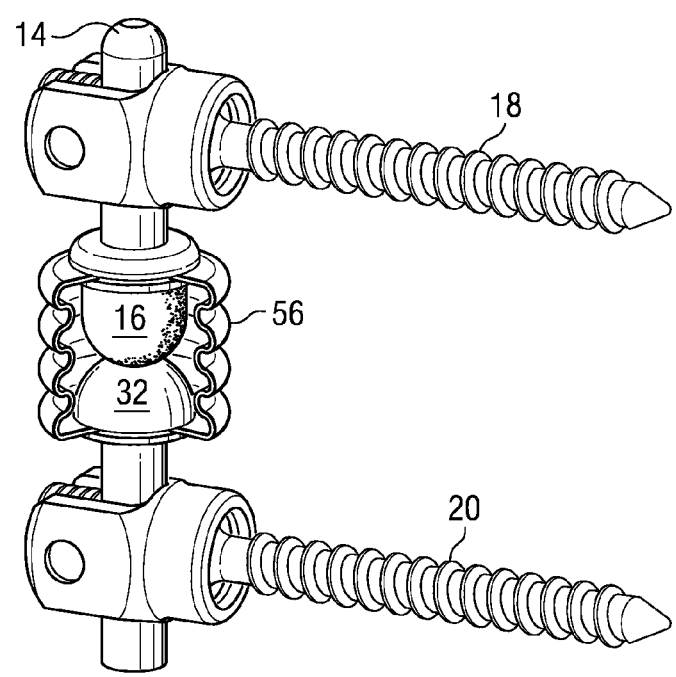
FIG. 21 is a perspective view, with a partial cutaway, of an embodiment of the present invention.

FIGS. 20 and 21 illustrate an embodiment of the present invention in which the bone anchor assemblies 18, 20 are not affixed to a substrate 44, 46.

In operation, a user will implant the first bone anchor assembly 18 and the second bone anchor assembly 20 in a first substrate 44 and a second substrate 46. The user positions the resilient element 12 such that the end portion 14 is connectable to a connector of the first bone anchor assembly 18 and the resilient portion 16 is engageable with the articulation surface 32 of the second bone anchor assembly 20 when the first bone anchor assembly 18 and the second bone anchor assembly 20 are moved closer to each other. The end portion is connected to the first bone anchor assembly. As noted above, in some embodiments the substrates 44, 46 are living and in some embodiments, the substrates 44, 46 are non-living. Implantation in living substrates, such as adjacent vertebrae, is to provide dynamic stabilization of the substrates. Implantation in non-living substrates could be for training, evaluation, development, or any other reason.

In one embodiment, the dynamic stabilization system 10 is implanted into a living patient using pedicle screws implanted into adjacent vertebrae via a posterior approach. Two systems 10 are generally placed bilaterally into adjacent vertebrae, but may also be a single system 10 placed unilaterally or one or wo systems 10 may be placed between non-adjacent vertebrae, such as a multi-level placement.

End portion 14 and resilient portion 16 may be arranged so that when the substrates are in a neutral position, the end portion 14 and the resilient portion 16 abut. Or end portion 14 and resilient portion 16 may be arranged so that when the substrates are in a neutral position, the end portion 14 and the resilient portion 16 are separated and do not abut. A neutral position would be, for example, when a vertebral motion segment is at rest.

When the first bone anchor assembly 18 and the second bone anchor assembly 20 are moved toward each other, such as during extension of a spinal motion segment to which the system 10 is attached, the resilient portion 16 and the articulation surface 32 abut and engage. As the first bone anchor assembly 18 and the second bone anchor assembly 20 continue to be moved toward each other, the resilient portion 16 resists such movement and deflects to provide a dampening effect on the movement. As the first bone anchor assembly 18 and the second bone anchor assembly 20 are moved away from each other, the resilient portion 16 substantially returns to its original shape.

As the first bone anchor assembly 18 and the second bone anchor assembly 20 are moved away from each other, whether the resilient portion 16 and articulation surface 32 are in abutment or not, the system 10 provides little or no resistance to this movement. Thus, if the system 10 is attached to a vertebral motion segment, there is little or no resistance to flexion of the spine. In some embodiments, as the first bone anchor assembly 18 and the second bone anchor assembly 20 are moved away from each other, the resilient portion 16 is separated from and no longer abuts, or engages, the articulation surface 32 of the second bone anchor assembly 20. The resilient portion 16 is configured to be separable from and unattached to the articulation surface 32.

Although reference is made herein to use of the dynamic stabilization system 10 with adjacent vertebrae, or a spinal motion segment, some embodiments include use of the dynamic stabilization system 10 of the present invention across non-adjacent vertebrae, or multi-level, or across more than a single spinal motion segment. The size and scale of the components, the placement of the bone anchor assemblies, etc., will be different than that for a single motion segment with adjacent vertebrae. Likewise, the size, scale, placement, etc., for use with a single motion segment with adjacent vertebrae will be different depending on what specific motion segment and adjacent vertebrae are involved. For example, the size and spacing for the L4-L5 motion segment may be different that the size and spacing for the L1-L2 motion segment and may also vary from patient to patient or substrate to substrate. These size, scale, placement, etc., differences can be determined by one of ordinary skill in the art without undue experimentation.

The form, shape, and the material of construction of the end portion 14, the resilient portion 16, the tether 26, the articulation surface 32, and connector 52 can be selected based on criteria chosen by the user without departing from the spirit or scope of the invention. Some suitable materials are included in U.S. Ser. No. 11/028,999, the disclosure of which is incorporated herein by reference in its entirety.

For example, the end portion 14 and articulation surface 32 may be made of metal, such as titanium. Examples of material that can be used for end portion 14 and articulation surface 32 include cobalt-chromium alloys, titanium alloys, nickel titanium alloys, and/or stainless steel alloys, any member of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); and/or cross-linked UHMWPE.

Resilient portion 16 may be of any shape, such as cylindrical, conical, or prismatic, including rectangular, pentagonal, hexagonal, etc. prisms, and may be made from a resorbable material. The resilient portion 16 is, for example, flexible, resilient, or elastic (inclusive) to permit motion of the spinal motion segment with which it is associated while providing a desired stabilization effect. The resilient portion 16 can be constructed such that it has a gradual or otherwise variable stiffness. Examples of material that can be used include any suitable biocompatible elastomer or polymer biomaterial, such as surgical latex, chloroprene, MIT's "biorubber" (glycerol and sebacic acid), polyethylene, polyester, polyurethane, urethane, polypropylene, polycarbonate urethane, silicone, or hydrogel, and combinations thereof. The resilient portion 16 can also be constructed in the form of a spring or any other shape exhibiting elastomeric properties from any suitable material. Examples of such material include cobalt-chromium alloys, titanium alloys, nickel titanium alloys, and/or stainless steel alloys.

The tether 26 and the connector 52 may be flexible or inflexible, elastic, inelastic, or semi-elastic and of any suitable form, such as a wire, rope, cord, band, belt, suture, bar, cable, solid or hollow rod, mesh, fabric, or other suitable form and may be a metal cable, such as a titanium or titanium alloy cable. The tether 26 can be single strand, multiple strands, braided, or combinations thereof and constructed of any suitable material, preferably a biocompatible material. Examples of possible materials include but is not limited to woven or non-woven polymers, such as polyester, polyethylene, or any member of the polyaryletherketone (PAEK) family such as polyetheretherketone (PEEK), carbon-reinforced PEEK, or polyetherketoneketone (PEKK), polysulfone; polyetherimide, polyimide, ultra-high molecular weight polyethylene (UHMWPE), and/or cross-linked UHMWPE; superelastic metals, such as nitinol; shape memory alloy, such as nickel titanium; resorbable synthetic materials, such as suture material, metals, such as stainless steel and titanium; synthetic materials, allograft material; and bioelastomer material.

Other embodiments include provision of a second articulation surface attached to the end portion 14 having the resilient portion 16 disposed between the second articulation surface and the end portion 14. The second articulation surface cooperates with the articulation surface 32, as described in co-pending application Ser. No. 12/422,606, the entire disclosure of which is hereby incorporated by reference herein.

Any combination of features from the embodiments described above is also within the spirit and scope of the invention and such combinations and configurations will be apparent to one of ordinary skill in the art without undue experimentation to accomplish the specific results and parameters of particular circumstances present or contemplated.

While the present invention has been illustrated by the above description of embodiments, and while the embodiments have been described in some detail, it is not the intention of the applicant to restrict or in any way limit the scope of the invention to such detail. For example, the relative positioning of the resilient element and the articulation surface described above can be switched. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general or inventive concept.

We claim:

1. A bone anchor-based spinal dynamic stabilization system, comprising:
   a. a first bone anchor assembly engageable with a first vertebra and comprising a cavity;
   b. a second bone anchor assembly engageable with a second vertebra and having an outer surface defining a semi-spherical articulation surface, the articulation surface being free of any gaps or protrusions;
   c. a resilient element comprising a resilient portion with a planar face that contacts the semispherical articulation surface and an end portion defined by an elongated protrusion configured for disposal in the cavity to engage the resilient element with the first bone anchor assembly; and
   d. at least one sheath having a proximal end and a distal end at least partially circumferentially surrounding and spaced from the articulation surface; wherein the sheath and the end portion are monolithic
   wherein the resilient element is configured to be separably engageable with the articulation surface of the second bone anchor assembly and is positioned between the first bone anchor assembly and the articulation surface of the second bone anchor assembly to resiliently resist the movement of the first bone anchor assembly and the second bone anchor assembly towards each other, wherein said bone anchor-based spinal dynamic stabilization system is configured to permit movement of said semi-spherical articulation surface between first, second and third positions;

wherein in said first position said semi-spherical articulation surface is freely disengaged from said resilient element;

wherein in said second position said semi-spherical articulation surface contacts said resilient element permitting movement between said first bone anchor and said second bone anchor relative to each other without compression of said resilient element, and wherein in said third position said semi-spherical articulation surface compresses said resilient element.

2. The dynamic stabilization system of claim 1, wherein the sheath is substantially flexible.

3. The dynamic stabilization system of claim 2, wherein the sheath is connected to the second bone anchor assembly.

4. The dynamic stabilization system of claim 3, wherein the sheath at least partially encloses the resilient portion and the articulation surface.

5. The dynamic stabilization system of claim 1, wherein the sheath is substantially inflexible.

6. The dynamic stabilization system of claim 5, wherein the sheath includes an inner surface defining an opening in the distal end, the opening having a width that is greater than a maximum width of the semi-spherical articulation surface such that the semi-spherical articulation surface can be removed from the sheath through the opening.

7. The dynamic stabilization system of claim 1, wherein the sheath is not connected to the second bone anchor assembly.

8. The dynamic stabilization system of claim 1, wherein the resilient portion is disposed between the sheath and the articulation surface.

9. The dynamic stabilization system of claim 1, further comprising a fixing element to fix the sheath to the second bone anchor assembly such that the sheath and the second bone anchor assembly are capable of being fixed to convert the dynamic stabilization system to a rigid system.

10. A bone anchor-based spinal dynamic stabilization system, comprising:
 a. a first bone anchor assembly engageable with a first vertebra and comprising a cavity;
 b. a resilient element comprising:
  i. an end portion for attachment to the first bone anchor assembly defined by an elongated protrusion configured for disposal in the cavity to engage the resilient element with the first bone anchor assembly,
  ii. a first articulation surface defined by a planar face; and
  iii. a resilient portion for dampening movement of the first articulation surface toward the end portion, the resilient portion disposed between the end portion and the first articulation surface;
 c. a sheath having a proximal end and a distal end at least partially circumferentially surrounding and spaced from the articulation surface; wherein the sheath and the end portion are monolithic and
 d. a second bone anchor assembly engageable with a second vertebra and having an outer surface defining a second articulation surface that is free of any gaps or protrusions and is configured to communicate with the first articulation surface, the second articulation surface having a convex shape;

wherein the first articulation surface is configured to be separably engageable with the second articulation surface and is positioned between the end portion of the first bone anchor assembly and the second articulation surface of the second bone anchor assembly; and wherein a planar face of the resilient portion engages the second articular surface, the resilient portion resiliently resisting the movement of the first bone anchor assembly and the second bone anchor assembly towards each other, wherein said bone anchor-based spinal dynamic stabilization system is configured to permit movement of said second articulation surface between first, second and third positions;

wherein in said first position said second articulation surface is freely disengaged from said resilient element;

wherein in said second position said second articulation surface contacts said resilient element permitting movement between said first bone anchor and said second bone anchor relative to each other without compression of said resilient element, and wherein in said third position said second articulation surface compresses said resilient element.

11. The spinal dynamic stabilization system of claim 10, further comprising a connector that secures the first articulation surface to the end portion, the connector attached to the end portion and the first articulation surface.

12. The spinal dynamic stabilization system of claim 11, wherein the connector passes through the resilient portion.

* * * * *